(12) United States Patent
Zlicar et al.

(10) Patent No.: US 9,150,518 B2
(45) Date of Patent: *Oct. 6, 2015

(54) PROCESS FOR PREPARING AMORPHOUS ROSUVASTATIN CALCIUM OF IMPURITIES

(75) Inventors: Marko Zlicar, Celje (SI); Zdenko Casar, Logatec (SI)

(73) Assignee: Lek Pharmaceuticals, D.D., Slovenia ( * ) Notice: Subject to any disclaimer, the term of this patent is extended or adjusted under 35 U.S.C. 154(b) by 1373 days.

This patent is subject to a terminal disclaimer.

(21) Appl. No.: 11/922,532

(22) PCT Filed: Jun. 22, 2006

(86) PCT No.: PCT/EP2006/006007
§ 371 (c)(1),
(2), (4) Date: Dec. 19, 2007

(87) PCT Pub. No.: WO2006/136407
PCT Pub. Date: Dec. 28, 2006

(65) Prior Publication Data
US 2009/0111839 A1    Apr. 30, 2009

(30) Foreign Application Priority Data
Jun. 24, 2005 (SI) .................. P200500188

(51) Int. Cl.
*C07D 239/42*    (2006.01)
(52) U.S. Cl.
CPC .................. *C07D 239/42* (2013.01)
(58) Field of Classification Search
CPC .................. C07D 239/42
See application file for complete search history.

(56) References Cited

U.S. PATENT DOCUMENTS

| | | | | |
|---|---|---|---|---|
| 5,312,914 A | * | 5/1994 | Sedelmeier et al. | 540/357 |
| 8,207,333 B2 | * | 6/2012 | Casar et al. | 544/242 |
| 2003/0114685 A1 | * | 6/2003 | Niddam-Hildesheim et al. | 548/530 |
| 2005/0059827 A1 | * | 3/2005 | Rukhman et al. | 548/254 |
| 2005/0124639 A1 | * | 6/2005 | Joshi et al. | 514/269 |
| 2007/0155765 A1 | * | 7/2007 | Sebek et al. | 514/275 |
| 2009/0036680 A1 | * | 2/2009 | Kumar et al. | 544/332 |

FOREIGN PATENT DOCUMENTS

| | | |
|---|---|---|
| EP | 0521471 | 1/1993 |
| WO | WO01/60804 | 8/2001 |
| WO | WO03/097614 | 11/2003 |
| WO | WO2004/014872 | 2/2004 |
| WO | WO2004/052867 | 6/2004 |
| WO | WO2005/023778 | 3/2005 |
| WO | WO2005/040134 | 5/2005 |
| WO | WO2005/042522 | 5/2005 |
| WO | WO2005/051921 | 6/2005 |
| WO | WO2005/054207 | 6/2005 |
| WO | WO2005/077916 | 8/2005 |
| WO | WO2005/077917 | 8/2005 |
| WO | WO2005/092867 | 10/2005 |

* cited by examiner

*Primary Examiner* — Sreeni Padmanabhan
*Assistant Examiner* — Jody Karol
(74) *Attorney, Agent, or Firm* — Luedeka Neely Group, P.C.

(57) ABSTRACT

A pure amorphous form of rosuvastatin calcium substantially free from alkali metal impurities is disclosed. A process of preparing a pure amorphous form of rosuvastatin calcium is disclosed, which comprises hydrolysis of $C_1$-$C_5$ alkyl esters of rosuvastatin, preferably tert-butyl ester of rosuvastatin, with an organic nitrogen base, e.g. guanidines, amidines, amines and quaternary ammonium hydroxides, in the presence of water, optionally containing aprotic solvent, following the conversion of thus obtained rosuvastatin salt with a source of calcium to obtain rosuvastatin calcium, which is then isolated. An alternative process is disclosed, which comprises the conversion of numerous novel ammonium salts of rosuvastatin, preferably tert-octylammonium salt of rosuvastatin, with the source of calcium to desired commercial rosuvastatin calcium. Rosuvastatin calcium is an inhibitor of HMG CoA reductase, useful in the treatment of hyperlipidemia, hypercholesterolemia and atherosclerosis.

10 Claims, 3 Drawing Sheets

PROCESS FOR PREPARING AMORPHOUS ROSUVASTATIN CALCIUM OF IMPURITIES

This application is the National Stage of International Application No. PCT/EP/2006/006007, filed on Jun. 22, 2006, which claims benefit under 35 U.S.C. §119(e) of Slovenia Patent application No. P200500188, filed on Jun. 24, 2005, the contents of both are incorporated herein by reference in their entirety.

FIELD OF THE INVENTION

The present invention relates to a process for the preparation of amorphous rosuvastatin calcium, substantially free of alkali metal impurities, via ammonium salts of rosuvastatin as intermediary compounds.

BACKGROUND OF THE INVENTION

Rosuvastatin is generic name for (+)-7-[4-(4-fluorophenyl)-6-isopropyl-2-(N-methyl-N-methylsulfonylamino)pyrimidin-5-yl]-(3R,5S)-dihydroxy-(E)-heptenoic acid administered in the therapy as its calcium salt as commercial drug, and illustrated in Formula 1 hereinafter, which compound is an inhibitor of the enzyme 3-hydroxy-3-methylglutaryl-coenzyme A reductase (HMG CoA reductase), useful in the treatment of hyperlipidemia, hypercholesterolemia and atherosclerosis. Rosuvastatin and the synthesis of rosuvastatin calcium was first described in patent EP-B-521 471; in the last two steps of the whole synthesis provided by hydrolysis of methyl ester of rosuvastatin (methyl rosuvastatin) in polar solvent, e.g. ethanol, in the presence of a base, e.g. sodium hydroxide, following by isolation of sodium salt of rosuvastatin and converting said sodium salt of rosuvastatin with a water soluble calcium salt under aqueous conditions to calcium salt of rosuvastatin. The process for the preparation of the intermediates described in EP-B-521 471 patent is incorporate herein by reference.

WO 2005/023778 describes a process for the preparation of rosuvastatin calcium by conversion of $C_1$ to $C_4$ alkyl ester of rosuvastatin, preferably tert-butyl ester of rosuvastatin with a base, preferably sodium hydroxide, in the presence of a $C_1$ to $C_4$ alcohol, preferably ethanol, to a solution of rosuvastatin salt, e.g. its sodium salt and converted said salt into rosuvastatin calcium by adding a source of calcium to said solution.

A novel crystalline form of rosuvastatin calcium can be prepared by crystallization of amorphous form of rosuvastatin calcium from a mixture of: (i) water and acetonitrile in the ratio of 1:1 by volume; (ii) water and acetone in the ratio of 1:1 by volume; or water, methanol and methyl tert-butyl ether in the ratio of 1:1:1 by volume, what is described in WO 2000/042024.

WO 01/60804 discloses certain novel amine salt with rosuvastatin, which may be prepared by addition of an appropriate amine or base to a solution of rosuvastatin acid in acetonitrile or ethyl acetate. Certain novel amine salts of rosuvastatin, preferably its crystalline methylammonium salt, may be used in the preparation of amorphous calcium salt of rosuvastatin, which process comprises sequential reaction of the crystalline methylammonium salt of rosuvastatin with sodium hydroxide, followed by a water soluble calcium salt, such as calcium chloride, under aqueous conditions. An approach is disclosed in WO 2005/051921 where rosuvastatin calcium salt is purified by conversion into isopropylammonium or cyclohexylammonium salt and back to calcium salt.

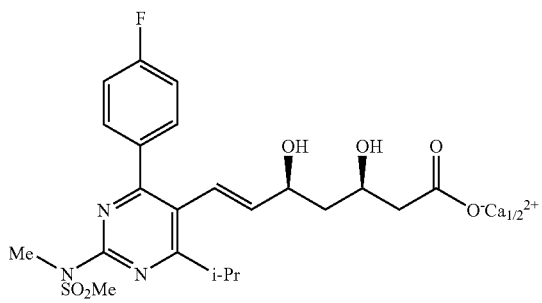

Formula 1

It is well known that alkali metal salts of organic acids are often hygroscopic what may cause problems at isolation. Indeed the isolation of sodium salt of rosuvastatin, which can be an intermediate in preparing rosuvastatin calcium salt, might be unrepeatable in yield and physical state what depends on the reaction conditions and evaporation of solvents, which is difficult to control. International publication WO 2005/23778 tried to avoid said problems without isolating rosuvastatin sodium salt by extraction of impurities from its aqueous solution into water immiscible solvent, but by using $C_1$ to $C_4$ alcohols as reaction medium a risk of conversion into specific impurities still existed. Namely, it is known that β-hydroxy acids in alcoholic alkali solution are submitted to dehydration what may lead after realkoxylation into special side products (see FIG. 1, Scheme 1, wherein R and $R_1$ independently denotes $C_1$ to $C_5$ alkyl group), O-alkyl derivatives of rosuvastatin, e.g. O-ethyl rosuvastatin.

Therefore a need for an efficient process for preparing pure amorphous rosuvastatin calcium, without any significant amounts of side products and in having the exact stoichimetric content without other alkali metal cation, still exists.

SUMMARY OF THE INVENTION

In a general aspect of the invention there is provided a pure amorphous form of rosuvastatin calcium of Formula 1 having a purity of more than 99.5%, preferably a purity of more than 99.8%, more preferably a purity of more than 99.9% as determined by HPLC area percentage, and free from any traces of alkali metal impurities.

In a first aspect the present invention provides a process for producing pure amorphous calcium salt of rosuvastatin, substantially free of alkali metal impurities, e.g. sodium cation impurity, which comprises:
  a) hydrolysis of $C_1$ to $C_5$ alkyl esters of rosuvastatin or rosuvastatin lactone with an organic nitrogen base in the presence of water, optionally containing aprotic solvent,
  b) converting thus obtained rosuvastatin salt of an organic nitrogen base with a source of calcium to obtain rosuvastatin calcium,
  c) isolating the pure amorphous calcium salt of rosuvastatin.

The starting ester may be methyl ester of rosuvastatin, preferably tert-butyl ester of rosuvastatin (tert-butyl rosuvastatin).

An organic nitrogen base is selected from the group consisting of guanidines, amidines, amines, quaternary ammonium hydroxides, unsubstituted or $C_1$ to $C_6$ alkyl substituted piperazines, morpholines, thiomorpholines, imidazolidines or adamantans.

Any aprotic solvent in step a) may be used, preferably tetrahydrofuran.

Any appropriate source of calcium may be used, preferably calcium chloride, calcium hydroxide, calcium acetate and calcium palmitate.

The process according to the invention may be performed in a solutions of an intermediary salts of rosuvastatin with organic nitrogen bases. Said salts are novel compounds, e.g. amine salts of rosuvastatin, not described in the prior art.

In another aspect of the invention rosuvastatin salts of an organic nitrogen bases may be isolated, optionally purified, e.g. by recrystallization, and used as intermediates in the preparation of the pure amorphous rosuvastatin calcium salt.

The desired pure amorphous rosuvastatin calcium salt is substantially free from any traces of alkali metal salt impurities, e.g. from sodium cation, containing in intermediary rosuvastatin sodium salt obtained according to prior art processes. Further is desired pure rosuvastatin calcium free of any O-alkyl derivatives of rosuvastatin, e.g. free of O-ethyl derivative of rosuvastatin, which may be obtained as side product according to prior art processes, performed in $C_1$ to $C_4$ alcoholic medium.

Amorphous rosuvastatin calcium prepared by the process according to the invention has at least 99.5% of chromatographic purity; moreover when using very pure starting $C_1$ to $C_5$ rosuvastatin ester more than 99.8% purity, even more, in some cases more than 99.9% of chromatographic purity of desired rosuvastatin calcium may be obtained.

The term "chromatographic purity" means purity as determined by area percentage HPLC ("High Pressure Liquid Chromatography").

In another aspect of the invention the amorphous rosuvastatin calcium may be prepared by conversion of the novel intermediary ammonium salts of rosuvastatin with the source of calcium. Intermediary ammonium salts of rosuvastatin may be obtained by contacting rosuvastatin free acid with an appropriate amine according to the procedure which comprises:

a) hydrolysis of $C_1$ to $C_5$ alkyl ester of rosuvastatin or rosuvastatin lactone with an alkali metal hydroxide in a mixture of an aprotic solvent and water,
b) washing the reaction mixture with water immiscible solvent,
c) acidifying aqueous solution of rosuvastatin alkali salt with an acid,
d) extraction of the resulted aqueous solution of rosuvastatinic acid into a water immiscible organic solvent,
e) adding an appropriate amine to the obtained extract containing rosuvastatinic acid to convert said rosuvastatinic acid into ammonium salt of rosuvastatin,
f) converting ammonium salt of rosuvastatin with a source of calcium to obtain rosuvastatin calcium,
g) isolation of amorphous rosuvastatin calcium.

The water immiscible solvent used in above steps b) and d) is selected from the group consisting of $C_2$ to $C_5$ alkyl esters, e.g. acetate esters, preferably ethyl acetate (AcOEt), isopropyl acetate (i-Pr acetate) and iso-butyl acetate, ethers, chlorinated hydrocarbons and cyclic hydrocarbons.

As acid for acidifying aqueous solution of rosuvastatin alkali salt in step c) of above process e.g. hydrochloric acid or phosphoric acid may be used.

The term "rosuvastatinic acid" ("rosuvastatin free acid") means (+)-7-[4-(4-fluorophenyl)-6-isopropyl-2-(N-methyl-N-methylsulfonylamino)pyrimidin-5-yl]-(3R,5S)-dihydroxy-(E)-6-heptenoic acid.

By using sodium hydroxide in step a) for cleavage of starting rosuvastatin esters according to above procedure purification and isolation of various isolable intermediary rosuvastatin salts with an appropriate amine may be performed after which the content of sodium cation impurity may be lowered, e.g. by washing the reaction mixture of step b) by water immiscible solvents, in the desired rosuvastatin calcium salt to less than 0.1% of sodium by weight.

Some of the novel ammonium salts of rosuvastatin were prepared in well defined forms, preferably as tert-octylammonium salt of rosuvastatin, which may be isolated in highly pure crystalline form and may be valuable as analytical standard for HPLC and other analyses.

The above described process of the first aspect of the invention by means of organic nitrogen bases cleavage of rosuvastatin $C_1$ to $C_5$ esters or lactone can be successfully applied for the preparation of other in the art known statins, preferably atorvastatin.

And in final aspect of the invention provides for a pharmaceutical formulation comprising rosuvastatin calcium prepared according to above described process and a method of treatment of hyperlipidemia, hypercholesterolemia and atherosclerosis, comprising the step of administering said pharmaceutical formulation to the mammal in need thereof.

BRIEF DESCRIPTION OF THE DRAWINGS

Further advantages of the invention are apparent by reference to the detailed description when considered in conjunction with the figures, wherein.

DETAILED DESCRIPTION OF THE INVENTION

Figure 1:
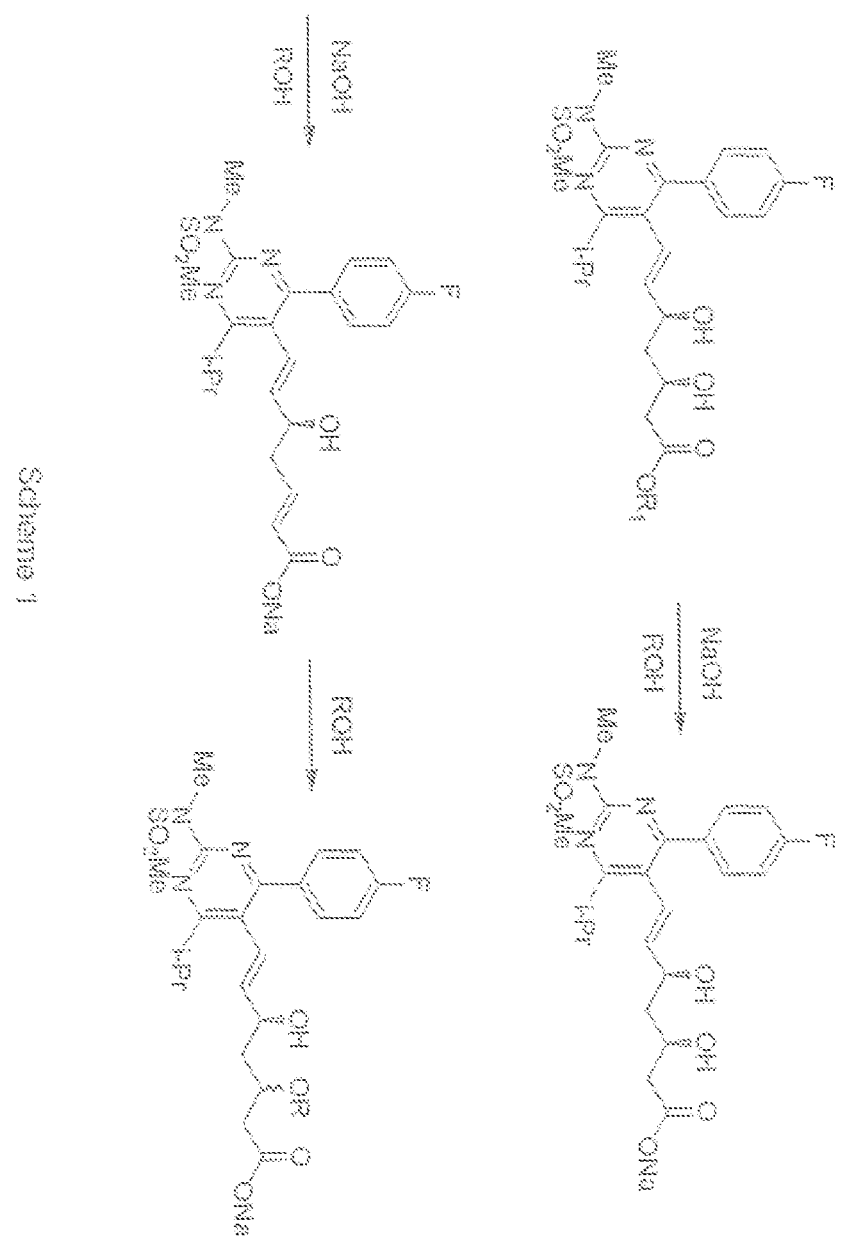
FIG. 1 is a diagram illustrating a reaction scheme for the preparation of a rosuvastatin salt.

An object of the present invention is to find a novel process for the preparation of pure amorphous rosuvastatin calcium, substantially free of sodium cation impurities or other alkali metal cation impurities and other impurities as well, which would avoid the use of alcohols, e.g. $C_1$ to $C_4$ alcohols as a reaction medium and the use of alkali metal hydroxides, e.g. sodium hydroxide, thus eliminating O-alkyl rosuvastatin impurities (see FIG. 1, Scheme 1), e.g. O-ethyl rosuvastatin derivative and obtaining rosuvastatin calcium free of any traces of sodium cation impurity or alkaline metal cation impurities, which may be present as impurities in rosuvastatin calcium, prepared according to the prior art processes.

Thus, the term "substantially free" means that the desired obtained amorphous rosuvastatin calcium is free of any traces of alkali metal impurities, e.g. sodium metal impurity.

Further is the object of the present invention to find a novel process which would enable easy and simple preparation and optionally isolation of intermediary novel rosuvastatin salt with organic nitrogen bases, e.g. novel ammonium salts of rosuvastatin, in good quality, and which would enable simple and easy conversion of said novel intermediary compounds to desired commercial amorphous rosuvastatin calcium.

We have unexpectedly and surprisingly found that above problem has been solved by hydrolysis of starting $C_1$ to $C_5$ alkyl esters of rosuvastatin (Formula 2) or rosuvastatin lactone (Formula 3), where instead of using $C_1$ to $C_4$ alcohols as protic solvent medium and strong inorganic alkali bases, e.g. sodium hydroxide, known in the prior art processes, hydrolysis take place in an aqueous solution of organic nitrogen bases. Namely, hydrolysis of starting $C_1$ to $C_5$ rosuvastatin esters in the presence of strong inorganic base, e.g. sodium hydroxide, according to the prior art processes, may result to incomplete conversion to desired rosuvastatin calcium. The consequence of incomplete conversion usually manifests in the presence of residual alkali metals, e.g. sodium cation, in the desired product. After using sodium hydroxide as a strong inorganic base, various amounts of residual sodium are found in the desired rosuvastatin calcium.

Formula 2

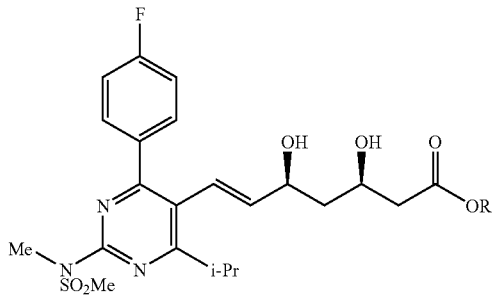

Formula 3

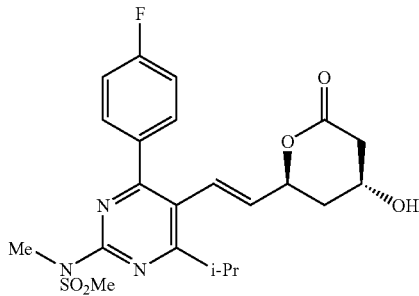

Residual sodium cation may be removed from rosuvastatin calcium by specific method, for instance the rosuvastatin calcium salt can be retreated by vigorous stirring in aqueous suspension, preferably by ultraturrax (Ultra-Turrax® is brand name of IKA Werke GmbH & Co., Staufen, Germany for dispersion making device with high speed rotation unit). Such methods eliminate sodium in a great extent, but none of the methods completely removes sodium from the desired rosuvastatin calcium.

The present invention provides the use of aqueous solution of organic nitrogen bases for cleavage of starting $C_1$ to $C_5$ alkyl ester of rosuvastatin or rosuvastatin lactone. Strong organic nitrogen bases selected from the group consisting of guanidines and amidines can be a method of choice. We have surprisingly found that also weak bases such as numerous amines if dissolved in water or in the mixtures of water and aprotic solvents, successfully cleft starting rosuvastatin esters if higher temperature is used. Moreover, we found out that by elevating temperature to 100° C. desired product did not neither degrade in considerable extent nor lead to appearance of corresponding amides of rosuvastatin.

According to the first aspect of the invention $C_1$-$C_5$ alkyl esters of rosuvastatin or rosuvastatin lactone, where alkyl denotes methyl, ethyl, n-propyl, iso-propyl, n-butyl, iso-butyl, tert-butyl, amyl or tert-amyl group, more preferably tert-alkyl esters, most preferably tert-butyl ester of rosuvastatin, are cleft in the solutions of organic nitrogen bases and water, optionally containing organic aprotic solvent, e.g. tetrahydrofuran.

The organic nitrogen base used according to the process of the invention is selected from the group consisting of:
a) guanidines of the formula:

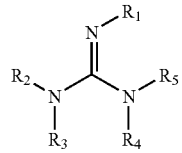

wherein each of $R_1$, $R_2$, $R_3$, $R_4$ and $R_5$ independently denotes a hydrogen atom, a straight chain or branched chain $C_1$-$C_6$ alkyl group or cyclic $C_1$-$C_6$ alkyl group or each pair of $R_1$, $R_2$, $R_3$, $R_4$ and $R_5$ independently denotes a $C_1$-$C_6$ alkylene group connection which forms a ring;
b) amidines of the formula:

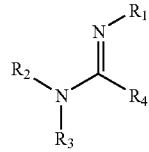

wherein each of $R_1$, $R_2$, $R_3$, and $R_4$ independently denotes a hydrogen atom, a straight chain or branched chain $C_1$-$C_6$ alkyl group or cyclic $C_1$-$C_6$ alkyl group or each pair of $R_1$, $R_2$, $R_3$, and $R_4$ independently denotes a $C_1$-$C_6$ alkylene group connection which forms a ring;
c) amines of the formula:

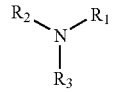

wherein each of $R_1$, $R_2$ and $R_3$ independently denotes a hydrogen atom, a straight chain or branched chain $C_1$-$C_6$ alkyl group or cyclic $C_1$-$C_{12}$ alkyl group, unsubstituted or substituted on one or more C-members of the alkyl chain with a radical selected from the group consisting of hydroxy, $C_1$-$C_6$ alkoxy, amino, $C_1$-$C_6$ alkylamino, di-$C_1$-$C_6$ alkylamino, phenyl, pyridinyl, $C_1$-$C_6$ alkylamino or each pair of $R_1$, $R_2$ and $R_3$ independently denotes $C_1$-$C_6$ alkylene connection which forms a ring;
d) quaternary ammonium hydroxides of formula $NR_1R_2R_3R_4{}^+OH^-$ wherein each of $R_1$, $R_2$, $R_3$ and $R_4$ independently denotes a hydrogen atom, a straight chain or branched chain $C_1$-$C_6$ alkyl group or cyclic $C_1$-$C_6$ alkyl group or each pair of $R_1$, $R_2$, $R_3$ and $R_4$ independently denotes $C_1$-$C_6$ alkylene group connection which forms a ring;
e) unsubstituted or $C_1$-$C_6$ alkyl N-substituted piperazines, morpholines, thiomorpholines, imidazolidines or adamantans.

A process for preparing ammonium salts of rosuvastatin by hydrolysis of $C_1$ to $C_5$ alkyl esters of rosuvastatin or rosuvastatin lactone with amines of above formula in the presence of water is shown on the following Scheme 2.

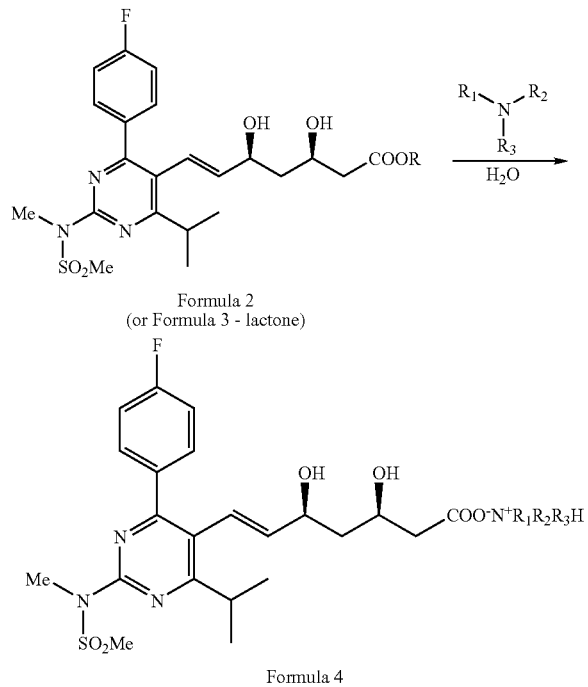

Scheme 2

Formula 2
(or Formula 3 - lactone)

Formula 4 wherein in Formula 2 R denotes $C_1$ to $C_5$ alkyl group and $R_1$, $R_2$ and $R_3$ denotes radicals as denoted in above formula of amines.

According to the process of the invention a preferred organic nitrogen base used from the guanidine group is N,N,N',N'-tetramethylguanidine, from the amidine group 1,5-diazabicyclo[4.3.0]non-5-ene (DBN) and 1,8-diazabicyclo[5.4.0]undec-7-ene (DBU), from the amine group n-propylamine iso-propylamine, N-methylcyclohexylamine, dicyclohexylamine, N-methyl-iso-propylamine, N,N-di-iso-propylamine, tert-butylamine, tert-octylamine (2,4,4-trimethylpent-2-ylamine), sec-butylamine and diethylamine.

According to the first aspect of the invention are starting $C_1$ to $C_5$ esters of rosuvastatin or rosuvastatin lactone, hydrolysed with organic nitrogen bases in the presence of water, optionally containing aprotic organic solvent (water content is more than 50% by volume, preferably more than 75% by volume). The hydrolysis is carried out at temperatures from 0° to 120° C. By said hydrolysis using strong organic nitrogen bases, e.g. guanidines and amidines is preferred temperature from 20° to 70° C., more preferred from 40° to 60°. By said hydrolysis using weak bases, e.g. amines, is the preferred temperature from 80° to 110° C., more preferred from 95° to 105° C., most preferred from 98° to 100° C. The hydrolysis of starting rosuvastatin esters according to the invention by applying volatile amines (boiling point bellow 120° C.) is carried out in tightly closed vessels at increased pressures.

In another aspect of the invention a novel intermediary ammonium salts of rosuvastatin may be isolated directly from the hydrolysis mixture by evaporation to dryness, optionally following by treatment with suitable solvent to induce solidification of the corresponding salt, which is further collected, e.g. by filtration. The choice of a solvent for solidification depends on physico-chemical properties of particular salt and can be selected but not limited from nitriles, esters, ethers or hydrocarbons. For example, solid isopropylammonium salt of rosuvastatin from acetonitrile and N-methylcyclohexylammonium salt of rosuvastatin from tert-butyl methyl ether are isolated by this manner.

In another aspect of the invention ammonium salts of rosuvastatin may be converted into rosuvastatin calcium salt without previous isolation of intermediary ammonium salt of rosuvastatin from the solution. Aqueous solution of rosuvastatin salt with an appropriate amine obtained after hydrolysis step is optionally washed by water immiscible solvents and further converted with calcium source to precipitate the desired pure amorphous rosuvastatin calcium.

The water immiscible solvents are selected from the group consisting of esters, ethers, chlorinated hydrocarbons or cyclic hydrocarbons, preferably more user-friendly solvents, e.g. $C_2$-$C_5$ acetate esters, e.g. ethyl acetate or cyclic hydrocarbons.

The source of calcium ion is selected from the group consisting of calcium halogenide, preferably calcium chloride, and another calcium source, e.g. calcium nitrate or calcium hydroxide, calcium salt of $C_1$-$C_{20}$ alkanoic acid, preferably calcium palmitate, calcium pivalate or calcium acetate.

In an another aspect of the invention the novel intermediary ammonium salts of rosuvastatin may be prepared from rosuvastatin free acid by the reaction with an appropriate amine.

The rosuvastatin free acid is prepared from a starting $C_1$ to $C_5$ ester of rosuvastatin or rosuvastatin lactone by reacting it with a suitable base, e.g. sodium hydroxide, in the presence of an aprotic solvent, optionally diluted with water, and subsequent addition of an acid, e.g. phosphoric acid or hydrochloric acid, to the solution of rosuvastatin sodium salt, thus obtaining rosuvastatin free acid.

The strong inorganic base used in the hydrolysis step may be sodium hydroxide or other alkali metal hydroxide, and the reaction is proceeded in the presence of water or in the presence of a mixture of aprotic solvents and water, such as a mixture of water and tetrahydrofuran, optionally under increased pressure. The obtained solution of rosuvastatin alkaline salt is optionally washed by water immiscible solvents selected from the group consisting of esters, ethers, chlorinated hydrocarbons or cyclic hydrocarbons, preferably from more user-friendly solvents such as acetate esters, cyclic hydrocarbons or alkanes, more preferably from ethyl acetate. The aqueous phase containing rosuvastatin alkaline salt is subsequently treated by a strong inorganic acid, preferably by phosphoric acid or hydrochloric acid.

Resulting rosuvastatinic acid (rosuvastatin free acid) is then extracted into water immiscible solvent and the obtained organic phase is converted to the ammonium salt of rosuvastatin by contacting with an appropriate amine. For the purpose of unification of water immiscible organic solvents, if said solvent is used to wash the reaction mixture, the same organic solvent may be used, for example an ester, preferably isopropyl acetate, for the reaction with an amine.

In a further procedure the organic extract (above mentioned solution of rosuvastatinic acid in water immiscible solvent, e.g. isopropyl acetate) is treated with an appropriate amine to obtain the corresponding ammonium salt of rosuvastatin. Alternatively, if said salt remains dissolved it can be precipitated by an addition of an antisolvent selected from other unpolar solvents, such as esters, ethers or hydrocarbons, optionally after concentration of the solution. In another alternative, the extracting solvent can be completely removed to isolate the solid ammonium salt of rosuvastatin or if oily further treated with suitable solvent to induce solidification of the corresponding salt, which is finally collected, e.g. by filtration. The solvent for the isolation of solid ammonium salt of rosuvastatin in all these alternatives strictly depends on solubility and physical properties of particular salt, but the preferred media are $C_2$-$C_5$ acetate esters and ethers, most preferred iso-propyl acetate and tert-butyl methyl ether.

According to this described aspect of the invention the following solid ammonium salts of rosuvastatin in good quality may be isolated:
N-methylcyclohexylammonium salt (99.6% area by HPLC);
cyclohexylammonium salt (99.71% area);
dicyclohexylammonim salt (99.82% area);
pyrrolidinium salt (99.71% area);
piperidinium salt (99.77% area);
morpholinium salt (99.51% area);
1-adamantylammonium salt (99.75% area);
tert-octylammonium salt (99.87% area).

Some of the isolated solid ammonium salts of rosuvastatin are good crystalline products, and can be isolated substantially pure. A characteristic example is tert-octylammonium salt of rosuvastatin, which can be isolated in two different pseudopolymorphs and be because of its purity conveniently used as an analytical standard.

From acetonitrile, optionally after washing with hexane an anhydrous crystalline form is isolated having diffraction angles in X-ray powder analysis, shown in Table 3, that is the invention is embodied in crystalline tert-octylammonium salt of rosuvastatin having X-Ray powder diffraction pattern characteristic with peaks at 8.0, 15.0, 17.7, 18.4, 18.8, 20.3, and 23.4±0, 2° 2θ and/or m.p. around 121° C.

From a mixture of acetonitrile and water a crystalline monohydrate is isolated having diffraction angles in X-ray powder analysis, shown in Table 4. The invention is embodied in crystalline monohydrate of tert-octylammonium salt of rosuvastatin having X-Ray powder diffraction pattern with characteristic peaks at 8.6, 16.5, 18.6, 19.1, and 19.7±0, 2° 2 Theta. Especially recrystallized anhydrous tert-octylammonium salt of rosuvastatin has stable defined structure, therefore is more suitable for use as an analytical standard than amorphous calcium salt with its hygroscopic properties and calcium assay variation. After determination of precise contain of rosuvastatin, for example by NMR or titration, the substance can be used as weighing standard compound in HPLC analyses of rosuvastatin.

The formed ammonium salts of rosuvastatin can be converted into rosuvastatin calcium salt by adding a source of calcium ions to said ammonium salt of rosuvastatin, preferably calcium acetate or calcium hydroxide, using water as a solvent.

The following examples illustrate the invention, but do not limit it in any way:

Analytical data in examples were achieved by the following hardware:

Melting points were determined in Kofler hot stage microscope and differential dynamic calorimeter Mettler Toledo DSC822e Powder X-ray diffraction spectra of the sample was recorded on Siemens D-5000 with reflexion technique: CuKα radiation, range from 2° to 37° 2 Theta, step 0.04° 2 Theta, integration time 1 sec. The accuracy in the difractograms is believed to be ±0.2, preferably ±0.1 2 Theta.

EXAMPLE 1

Hydrolysis of Tert-butyl Ester of Rosuvastatin in Aqueous Solution of Amines 7.5 g of tert-butyl ester of rosuvastatin
38 ml of demineralized water
2 to 5 equivalents of amine The reactants and water as the solvent are stirred in the autoclave from 98° to 100° C. for 1 to 4 hours. The reaction mixture is sampled and analyzed by HPLC ("High Pressure Liquid Chromatography") to find out the completion of reaction. Results are shown in Table 1.

TABLE 1

| Amine | Rosuvastatin salt with amine area % | Rosuvastatin tert-butyl ester, area % | Hydrolysis time from 95° to 100° C. |
|---|---|---|---|
| N-methyl-N-(iso-propyl)-amine | 98.9% | 0% | 2 h |
| iso-propylamine | 97.7% | 0% | 3 h |
| diethylamine | 98.4% | 0% | 3.5 h |
| N,N-di(iso-propyl)amine | 98.6% | 0.05% | 3 h |
| tert-butylamine | 98.4% | 0% | 4 h |
| sec-butylamine | 94.5% | 1.0% | 4 h |

EXAMPLE 2

Hydrolysis of Rosuvastatin Lactone in Aqueous Solution of N-methylcyclohexylamine 0.5 g of rosuvastatin lactone
0.5 ml of N-methylcyclohexylamine
3.0 ml of demineralized water The reactants and the solvent are stirred 1 hour at 90° C. forming clear solution and analysed as described in Example 1. HPLC analysis shows total consumption of the starting lactone.

EXAMPLE 3

Hydrolysis of Tert-butyl Ester of Rosuvastatin in a Solution of Strong Organic Nitrogen Bases The solution of tert-butyl ester of rosuvastatin in a mixture of a base, tetrahydrofuran and water in the ratio of 1:6:15 by volume is stirred at 50° C. for few hours. The reaction mixture is sampled and analysed by HPLC to find out the completion of reaction. Results are shown in Table 2.

TABLE 2

| Amine | Rosuvastatin salt with amine area % | Rosuvastatin tert-butyl ester, area % | Hydrolysis time and temperature |
|---|---|---|---|
| N,N,N'N'-tetramethylguanidine | 97.9% | 0% | 2 h (50° C.) |
| DBU | 97.8% | 0% | 2 h (50° C.) |
| DBN | 97.4% | 0% | 2 h (50° C.) |
| Tetramethylammonium hydroxide | 99.5% | 0% | 1 h (40-45° C.) |

EXAMPLE 4

Preparation of Iso-propylammonium Salt of Rosuvastatin 7.2 g of tert-butyl ester of rosuvastatin
35 ml of demineralized water
4.5 ml of iso-propylamine The reactants and water as the solvent are stirred in the autoclave from 98° to 100° C. for 2 hours. The solution formed is then allowed to cool to room temperature and some very little amount of solid impurities is filtered off. Filtrate is washed twice with 20 ml of iso-propyl acetate and the aqueous phase is then evaporated under reduced pressure at 70° C. and 15 mbar to remove solvents and iso-propylamine. 7.15 g of white solid residue of rosuvastatin iso-propylammonium salt is collected.

This amount is added to 70 ml acetonitrile and the suspension formed is heated under reflux (80° C.) for 1 h. Then, it is left for 2 h at 0° C. Subsequently, the product is separated by filtration. Yield: 6.7 g of white crystals of the pure product (>99.9% area, HPLC)

$^1$H-NMR: (CD$_3$OD): 1.29 (12H, d, J=7 Hz), 1.48-1.56 (1H, m), 1.62-1.72 (1H, m), 2.25 (1H, dd, J$_1$=14 Hz, J$_2$=7.6 Hz), 2.34 (1H, dd, J$_1$=14 Hz, J$_2$=4.9 Hz), 3.39 (1H, h, J=7 Hz), 3.51 (1H, h, J=7 Hz), 3.52 (3H, s), 3.53 (3H, s), 3.92-4.00 (1H, m), 4.33-4.40 (1H, m), 5.57 (1H, dd, J$_1$=16 Hz, J$_2$=6 Hz), 6.62 (1H, dd, J$_1$=16 Hz, J$_2$=1.2 Hz), 7.14-7.22 (1H, m), 7.69-7.75 (1H, m).

Analogously, tert-butylammonium salt of rosuvastatin is prepared with essentially the same yield:

$^1$H-NMR: (CD$_3$OD): 1.29. (6H, d, J=7 Hz), 1.35. (9H, s), 1.48-1.56. (1H, m), 1.62-1.72. (1H, m), 2.25. (1H, dd, J$_1$=15 Hz, J$_2$=7.6 Hz), 2.34. (1H, dd, J$_1$=15 Hz, J$_2$=4.9 Hz), 3.51. (1H, h, J=7 Hz), 3.52. (3H, s), 3.53. (3H, s), 3.92-4.00. (1H, m), 4.33-4.40. (1H, m), 5.57. (1H, dd, J$_1$=16 Hz, J$_2$=6 Hz), 6.62. (1H, dd, J$_1$=16 Hz, J$_2$=1.2 Hz), 7.14-7.22. (1H, m), 7.69-7.75. (1H, m).

EXAMPLE 5

Preparation of N-methylcyclohexylammonium Salt of Rosuvastatin 50 g of tert-butyl ester of rosuvastatin
225 ml of demineralized water
25 ml of N-methylcyclohexylamine The reactants and water as the solvent are stirred in the autoclave from 98° to 100° C. for 3 hours. The solution formed is then allowed to cool to room temperature, 150 ml of additional demineralized water and 20 ml tetrahydrofurane are added and some very little amount of solid impurities is filtered off. The resulting solution is then washed with 2×200 ml methylcyclohexane and the aqueous phase is evaporated under reduced pressure at 70° C. and 15 mbar to remove solvents and the N-methylcyclohexylamine. 50 ml toluene and 70 ml ethyl acetate are added and evaporated again to remove as much water as possible. To the oily residue 250 ml tert-butyl methyl ether is added and the mixture is digested forming white suspension. After cooling it at 0° C. for 12 hours, the suspension is filtered and washed with 60 ml tert-butyl methyl ether and dried on the filter. Yield: 50.8 g of white solid of N-methylcyclohexylammonium salt of rosuvastatin.

EXAMPLE 6

Preparation of N-methylcyclohexylammonium Salt of Rosuvastatin from N,N,N',N'-tetramethylguanidine Salt of Rosuvastatin 5.0 g of tert-butyl ester of rosuvastatin
1.4 ml of N,N,N',N'-tetramethylguanidine
25 ml of demineralized water
10 ml of tetrahydrofuran The reactants and solvents are stirred at 50° C. for 2 h. The solution formed is then allowed to cool to room temperature and washed twice with 40 ml of methylcyclohexane. The aqueous phase is partially evaporated to 25 g of total weight of the residue. 0.1 g of charcoal is added to aqueous phase and resulting suspension is stirred for 30 minutes. Charcoal and some solid impurities are filtered off and filtrate is diluted to 30 ml of total volume.

To 30 ml of the obtained solution 40 ml tert-butyl methyl ether is added 1.3 ml of 85% phosphoric acid in 5 ml of water and the resulting mixture is stirred for 15 minutes. A two-phase system is formed. Organic layer is separated and washed with 5 ml of water and dried with 5 g of anhydrous magnesium sulphate for 2 h. Magnesuim sulphate is then separated by filtration.

To filtrate is then added 1.5 ml N-methylcyclohexylamine and the reaction mixture is stirred for 2 hours at room temperature and then it is left resting at 0° C. for 12 hours. White precipitate of N-methylcyclohexylammonium salt of rosuvastatin is filtered off and washed with 5 ml of tert-butyl methyl ether and dried on the filter for 2 hours. Yield: 4.04 g of the title product (99.6% area, HPLC)

$^1$H-NMR: (CD$_3$OD): 1.10-1.45 (12H, m), 1.31 (d, J=7 Hz), 1.48-1.56 (1H, m), 1.62-1.72 (1H, m), 1.82-1.90 (2H, m), 2.03-2.10 (2H, m), 2.25 (1H, dd, J$_1$=14 Hz, J$_2$=7.6 Hz), 2.34 (1H, dd, J$_1$=14 Hz, J$_2$=4.9 Hz), 2.62 (3H, s), 2.85-2.97 (1H, m), 3.51 (1H, h, J=7 Hz), 3.52 (3H, s), 3.54 (3H, s), 3.92-3.97 (1H, m), 4.33-4.40 (1H, m), 5.56 (1H, dd, J$_1$=16 Hz, J$_2$=6 Hz), 6.62 (1H, dd, J$_1$=16 Hz, J$_2$=1.2 Hz), 7.14-7.22 (1H, m), 7.69-7.75 (1H, m).

EXAMPLE 7

General Procedure for Preparing Isolated Ammonium Salts of Rosuvastatin 5 g of tert-butyl ester of rosuvastatin
1.75 ml of 8 M NaOH
25 ml of demineralized water
10 ml of tetrahydrofuran The reactants and the solvents are stirred from 50° to 55° C. for 1 hour. The solution formed is then allowed to cool to room temperature and washed with 50 ml methylcyclohexane yielding 33 ml of aqueous solution of sodium salt of rosuvastatin.

To 33 ml of sodium rosuvastatinate solution prepared in the above described experiment is added 1.3 ml 85% phosphoric acid, previously dissolved in 5 ml of water. Reaction mixture is extracted with 40 ml of iso-butyl acetate. Organic layer is separated off and dried with 5 g of anhydrous magnesium sulphate. Drying agent is filtered off and washed with 10 ml iso-butyl acetate obtaining 52 ml of filtrate containing rosuvastatinic acid, which is divided into smaller portions for preparing various ammonium salts.

To 5 ml of the obtained solution 1.5 equivalents of appropriate amine and 5 ml tert-butyl methyl ether are added. Rosuvastatin substituted ammonium salt is filtered off and dried on filter. The following solid salts are prepared:

cyclohexylammonium salt of rosuvastatin: 0.45 g, 99.71% area by HPLC;

$^1$H-NMR: (CD$_3$OD): 1.10-1.45 (12H, m), 1.31 (6H, d, J=7 Hz), 1.48-1.56 (1H, m), 1.62-1.72 (1H, m), 1.80-1.87 (2H, m), 1.97-2.03 (2H, m), 2.25 (1H, dd, J$_1$=14 Hz, J$_2$=7.6 Hz), 2.34 (1H, dd, J$_1$=14 Hz, J$_2$=4.9 Hz), 2.98-3.09 (1H, m), 3.51 (1H, h, J=7 Hz), 3.52 (3H, s), 3.54 (3H, s), 3.92-3.97 (1H, m), 4.33-4.40 (1H, m), 5.56 (1H, dd, J$_1$=16 Hz, J$_2$=6 Hz), 6.62 (1H, dd, J$_1$=16 Hz, J$_2$=1.2 Hz), 7.14-7.22 (2H, m), 7.69-7.75 (1H, m);

dicyclohexylammonim salt of rosuvastatin: 0.35 g, 99.82% area;

$^1$H-NMR: (CD$_3$OD): 1.12-1.76 (20H, m), 1.29 (d, J=7 Hz), 1.48-1.56 (1H, m), 1.62-1.72 (1H, m), 1.83-1.92 (4H, m), 2.01-2.09 (4H, m), 2.25 (1H, dd, J$_1$=14 Hz, J$_2$=7.6 Hz), 2.34 (1H, dd, J$_1$=14 Hz, J$_2$=4.9 Hz), 3.07-3.17 (2H, m), 3.51 (1H, h, J=7 Hz), 3.52 (3H, s), 3.54 (3H, s), 3.92-3.97 (1H, m), 4.33-4.40 (1H, m), 5.56 (1H, dd, J$_1$=16 Hz, J$_2$=6 Hz), 6.62 (1H, dd, J$_1$=16 Hz, J$_2$=1.2 Hz), 7.14-7.22 (2H, m), 7.69-7.75 (2H, m);

pyrrolidinium salt of rosuvastatin: 0.28 g, 99.71% area,
$^1$H-NMR: (CD$_3$OD): 1.29 (6H, d, J=7 Hz), 1.48-1.56 (1H, m), 1.62-1.72 (1H, m), 1.96-2.01 (4H, m), 2.25 (1H, dd, J$_1$=14 Hz, J$_2$=7.6 Hz), 2.34 (1H, dd, J$_1$=14 Hz, J$_2$=4.9 Hz), 3.20-3.25 (4H, m), 3.51 (1H, h, J=7 Hz), 3.52 (3H, s), 3.54 (3H, s), 3.92-3.97 (1H, m), 4.33-4.40 (1H, m), 5.56 (1H, dd, J$_1$=16 Hz, J$_2$=6 Hz), 6.62 (1H, dd, J$_1$=16 Hz, J$_2$=1.2 Hz), 7.14-7.22 (2H, m), 7.69-7.75 (2H, m);

piperidinium salt of rosuvastatin: 0.28 9, 99.77% area;
$^1$H-NMR: (CD$_3$OD): 1.29 (6H, d, J=7 Hz), 1.48-1.56 (1H, m), 1.62-1.81 (7H, m), 2.25 (1H, dd, J$_1$=14 Hz, J$_2$=7.6 Hz), 2.34 (1H, dd, J$_1$=14 Hz, J$_2$=4.9 Hz), 3.09-3.13 (4H, m), 3.51 (1H, h, J=7 Hz), 3.52 (3H, s), 3.54 (3H, s), 3.92-3.97 (1H, m), 4.33-4.40 (1H, m), 5.56 (1H, dd, J$_1$=16 Hz, J$_2$=6 Hz), 6.62 (1H, dd, J$_1$=16 Hz, J$_2$=1.2 Hz), 7.14-7.22 (1H, m), 7.69-7.75 (2H, m);

morpholinium salt of rosuvastatin: 0.30 g, 99.51% area;
$^1$H-NMR: (CD$_3$OD): 1.29 (6H, d, J=7 Hz), 1.49-1.57 (1H, m), 1.62-1.72 (1H, m), 2.25 (1H, dd, J$_1$=14 Hz, J$_2$=7.6 Hz), 2.34 (1H, dd, J$_1$=14 Hz, J$_2$=4.9 Hz), 3.12-3.16 (4H, m), 3.51 (1H, h, J=7 Hz), 3.52 (3H, s), 3.53 (3H, s), 3.81-3.85 (4H, m), 3.92-4.00 (1H, m), 4.33-4.40 (1H, m), 5.57 (1H, dd, J$_1$=16 Hz, J$_2$=6 Hz), 6.62 (1H, dd, J$_1$=16 Hz, J$_2$=1.2 Hz), 7.14-7.22 (2H, m), 7.69-7.75 (1H, m);

1-adamantylammonium salt of rosuvastatin: 0.66 g, 99.75% area;
$^1$H-NMR: (CD$_3$OD): 1.29 (6H, d, J=7 Hz), 1.48-1.56 (1H, m), 1.62-1.85 (16H, m), 2.15 (3H, s (broad)), 2.25 (1H, dd, J$_1$=14 Hz, J$_2$=7.6 Hz), 2.34 (1H, dd, J$_1$=14 Hz, J$_2$=4.9 Hz), 3.51 (1H, h, J=7 Hz), 3.52 (3H, s), 3.54 (3H, s), 3.92-3.97 (1H, m), 4.33-4.40 (1H, m), 5.56 (1H, dd, J$_1$=16 Hz, J$_2$=6 Hz), 6.62 (1H, dd, J$_1$=16 Hz, J$_2$=1.2 Hz), 7.14-7.22 (2H, m), 7.69-7.75 (1H, m).

EXAMPLE 8

Preparation of N-cyclohexylammonium Salt of Rosuvastatin 10 g tert-butyl ester of rosuvastatin
3.5 ml 8 M NaOH
50 ml demineralized water
20 ml tetrahydrofuran The reactants and the solvents are stirred from 50° to 55° C. for 1 hour. The solution formed is then allowed to cool to room temperature and washed with 100 ml methylcyclohexane yielding 66 ml of aqueous solution of sodium rosuvastatinate.

To 33 ml of the obtained solution is added 1.3 ml 85% phosphoric acid in 5 ml demineralized water. Rosuvastatinic acid is extracted with 40 ml iso-propyl acetate. 4.7 g of anhydrous magnesium sulphate and 0.5 g charcoal is added to organic phase and suspension is stirred for 45 min. Magnesium sulphate and charcoal are filtered off yielding 41 ml of filtrate.

16 ml of the filtrate is separated and treated by addition of 0.5 ml of cyclohexylamine in 8 ml of iso-propyl acetate during stirring and rosuvastatin cyclohexylammonium salt precipitate instantaneously as white solid. It is separated by filtration, precipitate is washed on the filter with 10 ml of iso-propyl acetate and dried on the filter yielding 1.34 g of the desired product (99.52% area, HPLC).

EXAMPLE 9

Preparation of Crystalline Rosuvastatin Tert-octylammonium Salt

Rosuvastatin tert-butyl ester (27.0 g, 50.2 mmol) is dissolved in 225 ml of a mixture of tetrahydrofuran and water in the ratio of 4:1 by volume. The clear solution is warmed to 30° C. and 8.0 M NaOH (6.75 ml, 54.0 mmol) is added portionwise. The reaction mixture is stirred at 30° C. for 2 hours giving a clear yellow solution. Then tetrahydrofuran is removed completely under the reduced pressure (20 mbar) at 40° C. The remaining aqueous solution is diluted with water to 225 ml and washed with ethyl acetate (3×90 ml). To a vigorously stirring solution of sodium rosuvastatinate is added dropwise HCl 37% (4.2 ml, 50.2 mmol) at ambient temperature.

The obtained white emulsion of rosuvastatin free acid is extracted with ethyl acetate (150 ml). After separation from the organic layer aqueous phase is additionally extracted with ethyl acetate (2×50 ml). Organic layers are combined and washed with water (3×30 ml). Then ethyl acetate is removed under reduced pressure (20 mbar) at 40° C. The residue is dissolved in a minimal amount of acetonitrile and the solvent is rapidly evaporated under reduced pressure (20 mbar) at 40° C. to give 25.48 g of the solid residue. This solid is then dissolved in acetonitrile (100 ml) to give a clear solution. To a vigorously stirring solution of rosuvastatin free acid is added dropwise tert-octylamine (6.83 g, 50.2 mmol) over 1 minute at ambient temperature. In less then 10 minutes white solid precipitates abundantly from the solution, which cause solidification of the mixture. This solid is then treated with 75 ml of a mixture of hexane and acetonitrile in the ratio of 1:2 mixture by volume to give a dense suspension. The white precipitate is filtered and dried in vacuum at 40° C. to give 27.6 g of a white powder. This powder is suspended in hexane (100 ml) and vigorously stirred for 1 hour at ambient temperature. The undissolved precipitate is collected by filtration, washed with hexane (50 ml) and dried in vacuum at 40° C. to give 27.4 g (89.4%) of rosuvastatin tert-octylammonium salt as white crystalline powder.

Melting point: 121° C. (DSC, onset)

Figure 2:
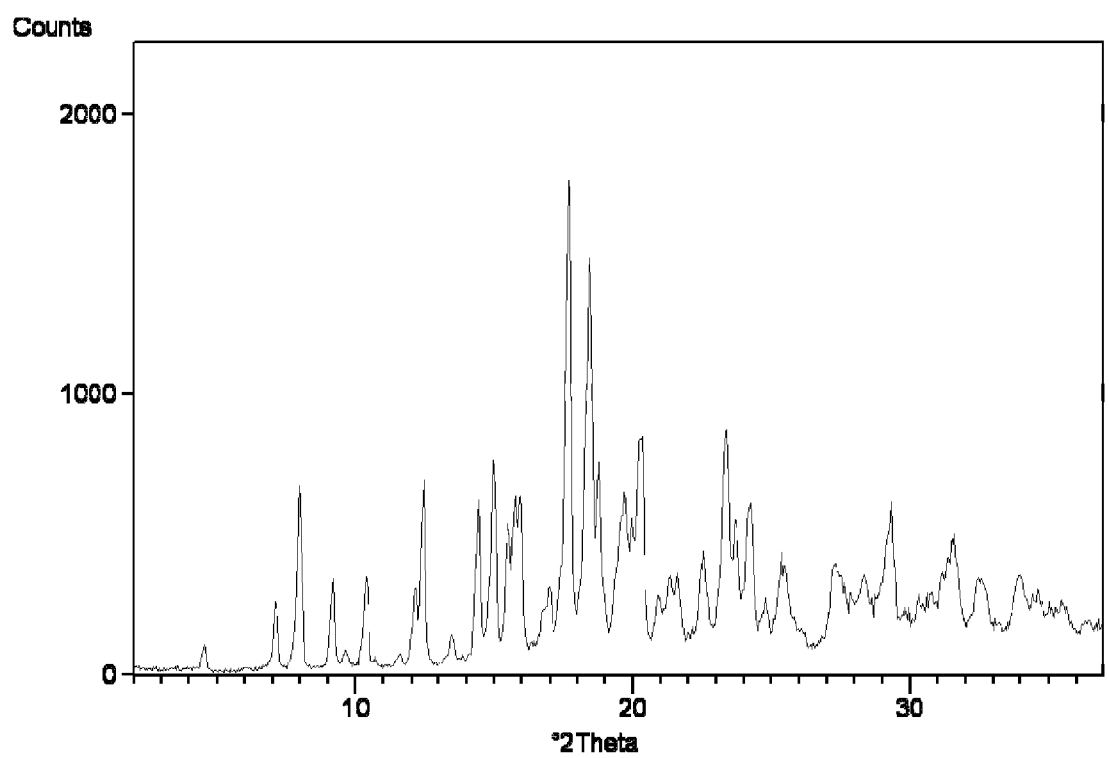
FIG. 2 is an X-ray powder diffraction diagram for a rosuvastatin salt prepared in accordance with one aspect of the present disclosure.

X-Ray powder analysis—diffraction angles (2 theta)—FIG. 2:

TABLE 3

| Angle (° 2θ) | Relative intensity (%) |
|---|---|
| 7.13 | 14.45 |
| 8.00 | 39.04 |
| 9.18 | 19.37 |
| 10.40 | 19.55 |
| 12.47 | 39.04 |
| 14.42 | 33.65 |
| 14.97 | 42.00 |
| 15.48 | 28.38 |
| 15.78 | 34.00 |
| 15.95 | 33.65 |
| 17.68 | 100.00 |
| 18.44 | 83.35 |
| 18.77 | 39.87 |
| 19.68 | 33.53 |
| 20.27 | 44.55 |
| 23.35 | 45.85 |
| 24.24 | 30.27 |
| 29.31 | 28.79 |

EXAMPLE 10

Preparation of Crystalline Rosuvastatin Tert-octylammonium Monohydrate Salt

Rosuvastatin tert-octylammonium salt (19.5 g) from Example 9 is dissolved in 429 ml of a mixture of acetonitrile and water in the ratio of 10:1 by volume at ambient temperature. The solution is left to stand at 6° C. for a few days. The white needles that crystallizes from the mixture are collected by filtration and dried in vacuum at 50° C. to give 10.48 g (53.7%) of crystalline rosuvastatin tert-octylammonium monohydrate salt as white needles.

Melting point: 129° C. (DSC, onset), dehydration 85° to 105° C.

Figure 3:
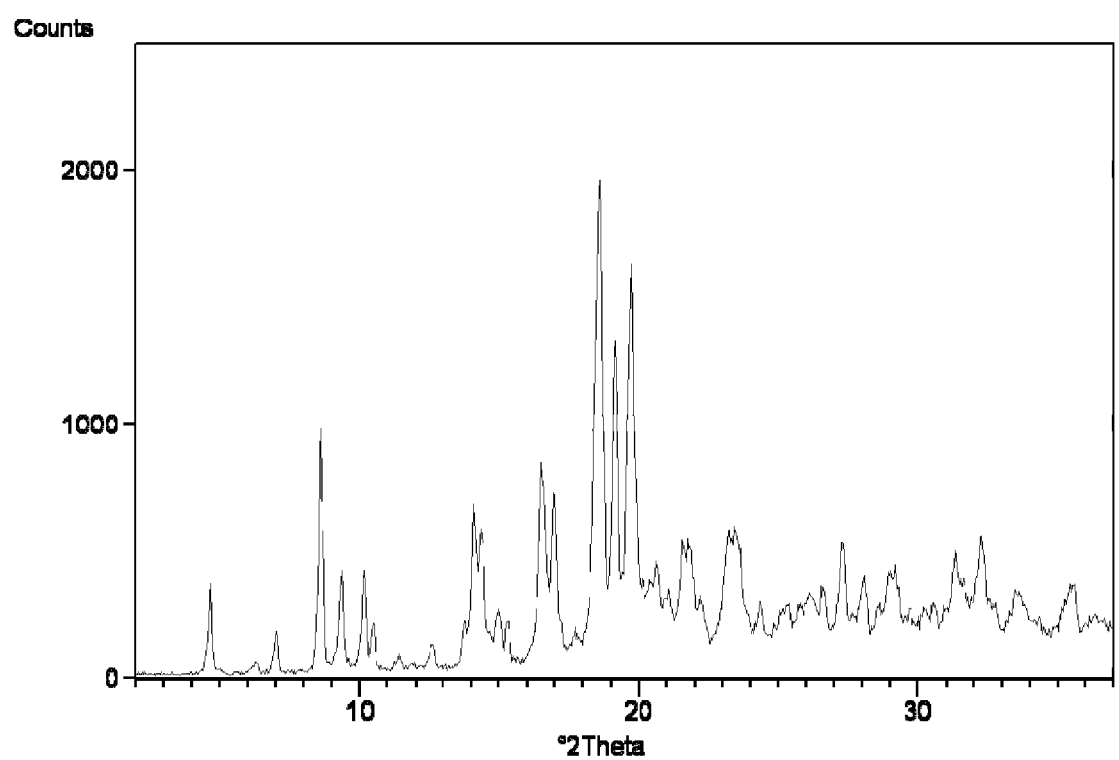
FIG. 3 is an X-ray powder diffraction diagram for a rosuvastatin salt prepared in accordance with another aspect of the present disclosure.

X-Ray powder analysis—diffraction angles (2 theta)—FIG. 3:

TABLE 4

| Angle (° 2θ) | Relative intensity (%) |
|---|---|
| 4.68 | 19.36 |
| 8.63 | 51.97 |
| 9.36 | 21.74 |
| 10.15 | 21.58 |
| 10.42 | 10.28 |
| 14.10 | 34.45 |
| 14.37 | 29.04 |
| 16.54 | 41.32 |
| 16.98 | 34.51 |
| 18.59 | 100.00 |
| 19.14 | 65.60 |
| 19.72 | 81.83 |
| 27.31 | 20.01 |

EXAMPLE 11

Preparation of Rosuvastatin Calcium from Tert-butyl Ester of Rosuvastatin via DBU Salt 1.0 g of tert-butyl ester of rosuvastatin
0.32 ml of 1,8-diazabicyclo[5.4.0]undec-7-ene (DBU)
5 ml of demineralized water
2 ml of tetrahydrofuran The reactants and the solvents are stirred at 50° C. for 2 h. The solution formed is then allowed to cool to room temperature and 2 ml demineralized water is added. Reaction mixture is washed twice with 10 ml methylcyclohexane. Combined organic phases are washed with 2 ml demineralized water. Combined aqueous phases are partially evaporated reducing original weight for 3.7 g. To remaining solution 0.25 ml of 4M calcium chloride is added during stirring and cooling on ice-bath for 15 minutes. White precipitate of rosuvastatin calcium is filtered off and washed with 1 ml demineralized water. 0.64 g of the desired amorphous product is collected after drying for 12 hours at room temperature in vacuum desiccator.

EXAMPLE 12

Preparation of Rosuvastatin Calcium from Rosuvastatin Lactone via DBU Salt 0.5 g rosuvastatin lactone
0.20 ml DBU
3.0 ml water The reactants and the solvent are stirred 1 hour at 90° C. forming clear solution. HPLC shows total consumation of the starting lactone.

Then, 0.16 g of calcium acetate monohydrate in 2 ml of water is added and the suspension formed is treated with ultraturrax at 15000 rpm for 5 minutes. The white precipitate of rosuvastatin calcium is separated by filtration. Yield: 0.42 g of the amorphous product.

EXAMPLE 13

Preparation of Rosuvastatin Calcium from Iso-propylammonium Salt of Rosuvastatin 7.5 g of tert-butyl ester of rosuvastatin
37 ml of water
3.5 ml of iso-propylamine
calcium hydroxide The reactants and the solvent are stirred in the autoclave from 95° to 100° C. for 2 hours. Reaction mixture is allowed to cool to room temperature and subsequently 20 ml of demi-water is added. Reaction mixture is washed twice with 37 ml methylcyclohexane. To aqueous phase 0.08 g charcoal is added and the resulting suspension is stirred for 45 minutes. Charcoal and some little amounts of solid impurities are filtered off. Resulting clear solution (containing rosuvastatin iso-propylammonium salt) is evaporated at reduced pressure to oily residue, which is diluted with water to 70 ml of total volume. To the obtained solution of rosuvastatin iso-propylammonium salt is added 2.0 g of moist calcium hydroxide paste (cca 50% content) and resulting suspension is stirred for 1 h at room temperature under nitrogen and for additional 15 min on ice-bath. White precipitate is then filtered off and washed with 8 ml of ice-cold demineralized water. The product is dried under vaccum at 60° C. for 3 hours. Yield: 6.15 g of amorphous rosuvastatin calcium.

EXAMPLE 14

Preparation of Rosuvastatin Calcium from Iso-propylammonium Salt of Rosuvastatin 2.0 g of rosuvastatin iso-propylammonium salt
13 ml of demineralized water
2.0 ml of 1M calcium acetate The reactants and the solvent are digested with ultraturrax for 2 minutes at 10000 rpm under nitrogen and then stirred 10 minutes with magnetic bar at 10° C. White precipitate is filtered off and washed with 2 ml demineralized water. It is dried 1 hour on the filter and 2 hours from 50° to 60° C. at 10 mbars. Yield: 1.67 g of amorphous rosuvastatin calcium (>99.8% area, HPLC, <0.1% sodium calculated on the content of calcium)

EXAMPLE 15

Preparation of Rosuvastatin Calcium from N-methylcyclohexylammonium Salt of Rosuvastatin 1.0 g rosuvastatin N-methylcyclohexylammonium salt
0.48 g of calcium palmitate
5.0 ml iso-butyl acetate The reactants and the solvent are stirred 5 minutes at 80° C. Gradually, 6 ml of methylcyclohexane is added within 5 minutes at 80° C. The reaction mixture is then stirred for 20 minutes at room temperature. Resulting precipitate is separated by filtration and washed on filter with 5 ml methylcyclohexane. 0.40 g of amorphous rosuvastatin calcium is collected (99.26% area, HPLC)

EXAMPLE 16

Preparation of Rosuvastatin Lactone 20.0 g rosuvastatin tert-butyl ester
6.5 ml 8M KOH
40 ml tetrahydrofuran
100 ml demineralized water The reactants and the solvents are stirred 1.5 hours from 40° to 45° C. hydrolysing starting rosuvastatin ester into its potassium salt. The clear solution formed is washed twice with 50 ml methylcyclohexane followed by filtration to remove some little amount of solid impurities. Then, the filtrate is treated with 100 ml ethyl acetate and 4.3 ml of 85% phosphoric acid forming two layers. The upper layer is separated and washed with 20 ml of water. To the organic phase is then added 1.0 ml of 85% phosphoric acid and the reaction mixture is heated 5 minutes on the water-bath of the rotavapor at 50° C. at atmospheric pressure. Then, the solvent is evaporated at reduced pressure. To the syrupy residue another 100 ml of ethyl acetate is added and the process of heating, evaporation and adding ethyl acetate is repeated three times. At last, the ethyl acetate solution of rosuvastatin lacton is washed with 20 ml of 5% solution of sodium bicarbonate and twice with 30 ml water. The solvent is evaporated at reduced pressure giving 17.0 g of syrupy residue, which crystallized on standing (91% area by HPLC).

By consecutive treatment with ultraturrax at 15000 rpm in 80 ml of tert-butyl methyl ether, filtration and recrystallization from isopropyl acetate/diisopropyl ether the purity is enhanced to 95% area.

The invention claimed is:

1. A process for producing pure amorphous rosuvastatin calcium which comprises:
   a) hydrolysis of one or more $C_1$ to $C_5$ alkyl esters of rosuvastatin or rosuvastatin lactone with an organic nitrogen base in the presence of a mixture consisting essentially of water and an aprotic solvent to produce a rosuvastatin salt of the base;
   b) converting the thus obtained rosuvastatin salt of organic nitrogen base with a source of calcium to obtain a reaction product mixture containing rosuvastatin calcium; and
   c) isolating pure amorphous rosuvastatin calcium, substantially free from any traces of alkali metal salt impurities, from the reaction product mixture,
   wherein the process avoids the use of alkali metal hydroxides.

2. A process according to claim 1, wherein the $C_1$ to $C_5$ alkyl ester of rosuvastatin includes tert-butyl rosuvastatin.

3. A process according to claim 1, wherein the organic nitrogen base includes one or more bases elected from the group consisting of:
   a) guanidines of the formula:

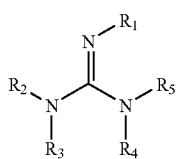

wherein each of $R_1$, $R_2$, $R_3$, $R_4$ and $R_5$ independently denotes a hydrogen atom, a straight chain or branched chain $C_1$-$C_6$ alkyl group or cyclic $C_1$-$C_6$ alkyl group or each pair of $R_1$, $R_2$, $R_3$, $R_4$ and $R_5$ independently denotes a $C_1$-$C_6$ alkylene group connection which forms a ring,
   b) amidines of the formula:

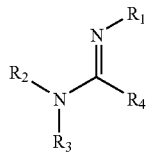

wherein each of $R_1$, $R_2$, $R_3$, $R_4$ and $R_5$ independently denotes a hydrogen atom, a straight chain or branched chain $C_1$-$C_6$ alkyl group or cyclic $C_1$-$C_6$ alkyl group or each pair of $R_1$, $R_2$, $R_3$, and $R_4$ independently denotes a $C_1$-$C_6$ alkylene group connection which forms a ring;
   c) amines of the formula

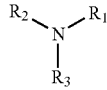

wherein each of $R_1$, $R_2$ and $R_3$ independently denotes a hydrogen atom, a straight chain or branched chain $C_1$-$C_6$ alkyl group or cyclic $C_1$-$C_{12}$ alkyl group, unsubstituted or substituted on one or more C-members of the alkyl chain with a radical selected from the group consisting of hydroxy, $C_1$-$C_6$ alkoxy, amino, $C_1$-$C_6$ alkylamino, di-$C_1$-$C_6$ alkylamino, phenyl, pyridinyl, $C_1$-$C_6$ alkylamino or each pair of $R_1$, $R_2$ and $R_3$ independently denotes $C_1$-$C_6$ alkylene group connection which forms a ring;
   d) quaternary ammonium hydroxides of formula:

$NR_1R_2R_3R_4{}^+OH^-$ wherein each of $R_1$, $R_2$, $R_3$ and $R_4$ independently denotes a hydrogen atom or chained, branched or cyclic $C_1$-$C_6$ alkyl group or each pair of $R_1$, $R_2$, $R_3$ and $R_4$ independently denotes $C_1$-$C_6$ alkylene connection which forms a ring and;
   e) unsubstituted or $C_1$-$C_6$ alkyl N-substituted piperazines, morpholines, thiomorpholines, imidazolidines or adamantans.

4. A process according to claim 1, wherein the organic nitrogen base is N,N,N'N'-tetramethylguanidine.

5. A process according to claim 1, wherein the organic nitrogen base is selected from the group consisting of 1,5-diazabicyclo[4.3.0]non-5-ene (DBN) and 1,8-diazabicyclo[5.4.0]undec-7-ene (DBU).

6. A process according to claim 1, wherein the organic nitrogen base is selected from the group consisting of isopropylamine, sec-butylamine, tert-butylamine, diethylamine, N,N-diisopropylamine, N-methyl-isopropylamine, N-methylcyclohexylamine.

7. A process according to claim 1, wherein the source of calcium is selected from the group consisting of calcium chloride, calcium nitrate, calcium hydroxide and calcium salt of $C_1$-$C_{20}$ alkanoic acid.

8. A process according to claim 7, wherein the calcium salt of $C_1$-$C_{20}$ alkanoic acid is selected from the group consisting of calcium palmitate, calcium pivalate and calcium acetate.

9. A process according to claim 1, wherein the aprotic solvent is tetrahydrofuran.

10. A process according to claim 3, wherein the amine and the $C_1$ to $C_5$ ester of rosuvastatin has a molar ratio from 2 to 5.

* * * * *